United States Patent [19]

Al-Ghatta

[11] Patent Number: 5,049,647

[45] Date of Patent: Sep. 17, 1991

[54] METHOD FOR THE REDUCTION OF IMPURITIES IN POLYESTER RESINS

[75] Inventor: Hussain A. Al-Ghatta, Fiuggi, Italy

[73] Assignee: Cobarr S.p.A., Anagni, Italy

[21] Appl. No.: 289,911

[22] Filed: Dec. 27, 1988

[51] Int. Cl.⁵ ............................................. C08G 63/89
[52] U.S. Cl. ................................. 528/272; 528/308.2; 528/308.4; 528/308.5; 528/483; 528/500; 525/437
[58] Field of Search .................. 528/272, 308.2, 308.4, 528/308.5, 483, 500; 525/437

[56] References Cited

U.S. PATENT DOCUMENTS

| | | | |
|---|---|---|---|
| 4,223,128 | 9/1980 | Halek et al. | 528/481 |
| 4,591,629 | 5/1986 | El-Ghatta et al. | 528/308.2 |
| 4,703,105 | 10/1987 | Allada | 528/483 |

*Primary Examiner*—John Kight, III
*Assistant Examiner*—Sam A. Acquah
*Attorney, Agent, or Firm*—Hedman, Gibson, Costigan & Hoare

[57] ABSTRACT

A method for purifying polyethyleneterephthalate reins by contacting the resins with an atmosphere containing carbon dioxide under supercritical conditions.

5 Claims, No Drawings

METHOD FOR THE REDUCTION OF IMPURITIES IN POLYESTER RESINS

The present invention relates to a method for the reduction of impurities which may be present in polymer materials based on polyethyleneterephthalate and polyethyleneterephthalate copolymers. The method according to the invention is particularly useful in the recycling of PET bottles.

The presence of acetaldehyde, for example, in the polyethyleneterephthalate granules is the cause of considerable problems both when the granules are intended for a polycondensation process in the solid state and when the already polycondensed granules are transformed into products, for example preformed parts or bottles.

Other unknown impurities may be present in the recycled PET resins especially when such resins derive from crushed PET bottles. As a matter of fact the PET bottles may have been improperly used in the household to contain liquids (acetone, acetic acid etc.) which diffuse in the bottle walls. These impurities restrict the reuse of the recycled PET for food applications.

The object of the present invention is to provide a method to purify PET resins and particularly recycled PET resins which are then used for food applications.

According to the invention, this object is achieved by virtue of the fact that the impurities are extracted from the PET resins by means of a supercritical fluid extraction using an atmosphere containing carbon dioxide as the supercritical fluid.

When polyethyleneterephthalate o polyethyleneterephthalate copolymer granules, films etc. are treated with supercritical carbon dioxide, a surprising reduction in the acetaldehyde content of the polymer is in fact noted, this content resulting either from the polymerisation process or from the polycondensation process.

Moreover, when recycled PET resins in the form of crushed bottles are treated with supercritical carbon dioxide, the supercritical fluid penetrates the surface of the crushed bottles and extract the impurities out of it.

A mixture of supercritical $CO_2$ and other supercritical fluids, especially water vapour, could be also used for the purification of the recycled PET.

In order to obtain the best results in the extraction of the impurities, pressures greater than 50 bars and temperatures between 31° and 245° C. are preferred.

The invention will be better understood with the aid of the following examples, whose content should not be understood as limiting of the scope of the present invention.

The impurities contents of the examples have been measured by the head space gas chromatographic method described in EP-A-86830340.5.

EXAMPLE 1

200 kg of polyethyleneterephthalate (PET) granules with an intrinsic viscosity of 0.78 (measured by the dissolution of 0.5 of PET in a mixture of 100 ml of phenol/tetrachloroethane) were treated in an autoclave at 300 bars for 2 hours at an average temperature of 115° C.

The rate at which acetaldehyde was generated, measured at 250° C., was 0.3 ppm/minute before the treatment, whilst after the treatment the rate of generation of acetaldehyde was reduced to 0.12 ppm/minute.

EXAMPLE 2

200 kg of PET granules with an intrinsic viscosity of 0.64 were treated in an autoclave containing carbon dioxide at 350 bars and 120° C., with a treatment time of 1.5 hours.

The acetaldehyde content was 110 ppm before treatment with supercritical carbon dioxide, whilst after treatment the content was reduced to 10 ppm.

According to a variant of the invention, the reduction of the acetaldehyde content with the use of supercritical carbon dioxide is further improved if water vapour is added to the carbon dioxide, preferably at a percentage which may vary between 1.1 and 10%. The following example describes the result of a test in which carbon dioxide was used with water vapour.

EXAMPLE 3

The same starting granules were used as in Example 2, and under the same conditions, the only difference being that 2% by weight of water vapour was added to the carbon dioxide. The acetaldehyde content after the treatment was 7 ppm.

EXAMPLE 4

Whilst examples 2 and S relate to a PET of low intrinsic viscosity (not yet subjected to polycondensation treatment), this last example, like Example 1 given above, relates to PET granules with an intrinsic viscosity of 0.78.

200 kg of PET were treated in an autoclave with carbon dioxide at 250 bars and 180° C for one hour. The acetaldehyde content before the treatment was 2 ppm, whilst after treatment the content was reduced to 0.8 ppm.

EXAMPLE 5

20 kg of recycled PET crushed-bottles, contaminated with acetone to a level of 10500 ppm, were treated in an autoclave containing $CO_2$ and 2% by weight of water vapour at 100 bars for 3 hours at an average temperature of 120° C. The gas chromatograph test of the powdered PET after the treatment shows no acetone. The intrinsic viscosity of PET crushed bottles before and after the treatment was respectively 0.787 and 0.778.

EXAMPLE 6

20 kg of recycled PET, contaminated with acetic acid to a level of 20100 ppm, were treated in an autoclave containing $CO_2$ at 250 bars for 2 hours at an average temperature of 130° C.

The gas chromatographic test shows a content of 3 ppm of acetic acid. There is no decrease in the intrinsic viscosity of the polymer before and after the treatment.

EXAMPLE 7

20 kg of recycled PET, contaminated with carbon tetrachloride to a level of 10250 ppm, were treated in an autoclave containing $CO_2$ at 280 bars for 5 hours at an average temperature of 150° C.

The gas chromatographic test of the powdered PET after the treatment shows no carbon tetrachloride.

There is no decrease in the intrinsic viscosity.

EXAMPLE 8

200 kg of recycled PET, contaminated with trichloroethane to a level of 500 ppm, were treated in an autoclave containing $CO_2$ at 150 bars for 3 hours at an average temperature of 145° C. The G.C. test shows a content of 2.3 ppm of trichloroethane. There is no decrease of intrinsic viscosity.

EXAMPLE 9

200 kg of recycled PET, contaminated with methyl benzoate to a level of 220 ppm, were treated in an autoclave containing $CO_2$ at 165 bars for 5 hours at an average temperature of 155° C.

The G.C. test shows a content of 1.2 ppm of methyl benzoate. There is no decrease of intrinsic viscosity.

Other tests were carried out filling PET bottles with fungicides, insecticides, deodorants, naphta and leaving them on a shelf for one week.

Then the bottles were emptied, crushed and treated according to the present invention. From the recycled PET, new bottles were obtained. These new PET bottles were filled with water that, after a storage of 3 months in the bottles at 40° C. has shown n appreciable taste, and it was not possible to detect any of the above impurities in the water.

I claim:

1. A method for purifying polyethyleneterephthalate based materials comprising: contacting the polyethyleneterephthalate materials with an atmosphere comprising carbon dioxide under supercritical conditions of temperature and pressure.

2. The method according to claim 1, wherein the materials are polyethyleneterephthalate resins.

3. The method according to claim 1, wherein the contacting step is carried out at a pressure greater than 50 bars.

4. The method according to claim 1, wherein the contacting step is carried out at a temperature between 31° C. and 245° C.

5. The method according to claim 1, wherein the atmosphere further comprises water vapour.

* * * * *